(12) United States Patent
Cox et al.

(10) Patent No.: US 8,198,590 B2
(45) Date of Patent: Jun. 12, 2012

(54) HIGH REFLECTANCE TERAHERTZ MIRROR AND RELATED METHOD

(75) Inventors: James Allen Cox, New Brighton, MN (US); Robert Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 864 days.

(21) Appl. No.: 12/261,911

(22) Filed: Oct. 30, 2008

(65) Prior Publication Data

US 2010/0108891 A1    May 6, 2010

(51) Int. Cl.
    *G01J 5/02*    (2006.01)
    *H01L 21/00*    (2006.01)
    *H01L 21/76*    (2006.01)

(52) U.S. Cl. ...... 250/341.8; 257/E21.002; 257/E31.032; 438/68; 438/458

(58) Field of Classification Search ............... 250/341.8, 250/208.1, 370.01; 257/E21.002, E21.032; 438/458, 68
See application file for complete search history.

(56) References Cited

U.S. PATENT DOCUMENTS

| | | | |
|---|---|---|---|
| 4,233,568 A | 11/1980 | Hamerdinger et al. | |
| 4,612,647 A | 9/1986 | Norvell | |
| 4,614,961 A | 9/1986 | Khan et al. | |
| 4,672,624 A | 6/1987 | Ford | |
| 4,870,224 A | 9/1989 | Smith et al. | |
| 4,973,131 A | 11/1990 | Carnes | |
| 5,022,745 A | 6/1991 | Zayhowski et al. | |
| 5,040,895 A | 8/1991 | Laurent et al. | |
| 5,135,304 A | 8/1992 | Miles et al. | |
| 5,146,465 A | 9/1992 | Khan et al. | |
| 5,278,435 A | 1/1994 | Van Hove et al. | |
| 5,408,319 A | 4/1995 | Halbout et al. | |
| 5,418,868 A | 5/1995 | Cohen et al. | |
| 5,450,053 A | 9/1995 | Wood | |
| 5,468,910 A | 11/1995 | Knapp et al. | |
| 5,512,750 A | 4/1996 | Yanka et al. | |
| 5,528,040 A | 6/1996 | Lehmann | |

(Continued)

FOREIGN PATENT DOCUMENTS

DE    3311808    10/1984

(Continued)

OTHER PUBLICATIONS

N. Amer, et al., "Terahertz wave propagation in one-dimensional periodic dielectrics", Applied Optics, vol. 45, No. 8, Mar. 10, 2006, p. 1857-1860.

(Continued)

*Primary Examiner* — David Porta
*Assistant Examiner* — Faye Boosalis

(57) ABSTRACT

A method includes forming a plurality of mirror periods, stacking the mirror periods, and bonding the mirror periods together to form a high reflectance mirror. At least one of the mirror periods is formed by bonding a first semiconductor layer to a first side of a film layer (where the film layer is formed on a second semiconductor layer), forming an opening through the second semiconductor layer to expose the film layer, and cutting through the first semiconductor layer, the film layer, and the second semiconductor layer. The first semiconductor layer could include a high resistivity silicon wafer, the film layer could include an oxide film, and the second semiconductor layer could include a silicon wafer. The high resistivity silicon wafer could be approximately 110 μm thick, and the silicon wafer could be approximately 125 μm thick. The opening through the second semiconductor layer could be 1.25 cm to 1.75 cm in width.

23 Claims, 10 Drawing Sheets

U.S. PATENT DOCUMENTS

| | | | |
|---|---|---|---|
| 5,550,373 A | 8/1996 | Cole et al. |
| 5,629,951 A | 5/1997 | Chang-Hasnain et al. |
| 5,677,538 A | 10/1997 | Moustakas et al. |
| 5,679,965 A | 10/1997 | Schetzina |
| 5,723,706 A | 3/1998 | Brasier et al. |
| 5,739,554 A | 4/1998 | Edmond et al. |
| 5,815,277 A | 9/1998 | Zare et al. |
| 5,834,331 A | 11/1998 | Razeghi |
| 5,835,231 A | 11/1998 | Pipino |
| 5,847,397 A | 12/1998 | Moustakas |
| 5,869,896 A | 2/1999 | Baker et al. |
| 5,900,650 A | 5/1999 | Nitta |
| 5,909,280 A | 6/1999 | Zavracky |
| 5,912,740 A | 6/1999 | Zare et al. |
| 5,915,051 A | 6/1999 | Damask et al. |
| 5,933,565 A | 8/1999 | Diebold |
| 5,960,025 A | 9/1999 | Thorland et al. |
| 6,040,895 A | 3/2000 | Haas |
| 6,080,988 A | 6/2000 | Ishizuya et al. |
| 6,084,682 A | 7/2000 | Zare et al. |
| 6,091,504 A | 7/2000 | Walker et al. |
| 6,094,267 A | 7/2000 | Levenson et al. |
| 6,115,122 A | 9/2000 | Bao et al. |
| 6,122,416 A | 9/2000 | Ooba et al. |
| 6,147,756 A | 11/2000 | Zavracky et al. |
| 6,208,798 B1 | 3/2001 | Morozov et al. |
| 6,233,052 B1 | 5/2001 | Zare et al. |
| 6,287,940 B1 | 9/2001 | Cole et al. |
| 6,295,130 B1 | 9/2001 | Sun et al. |
| 6,296,779 B1 | 10/2001 | Clark et al. |
| 6,310,904 B1 | 10/2001 | Thorland et al. |
| 6,324,192 B1 | 11/2001 | Tayebati |
| 6,335,669 B1 | 1/2002 | Miyazaki et al. |
| 6,377,350 B1 | 4/2002 | Paldus et al. |
| 6,380,531 B1 | 4/2002 | Sugihwo et al. |
| 6,384,953 B1 | 5/2002 | Russell et al. |
| 6,404,648 B1 | 6/2002 | Slupe et al. |
| 6,406,578 B1 | 6/2002 | Schober et al. |
| 6,421,127 B1 | 7/2002 | McAndrew et al. |
| 6,424,419 B1 | 7/2002 | Tazartes et al. |
| 6,438,149 B1 * | 8/2002 | Tayebati et al. ............ 372/45.01 |
| 6,452,680 B1 | 9/2002 | Paldus et al. |
| 6,466,322 B1 | 10/2002 | Paldus et al. |
| 6,483,130 B1 | 11/2002 | Yang et al. |
| 6,492,726 B1 | 12/2002 | Quek et al. |
| 6,507,107 B2 | 1/2003 | Vaiyapuri |
| 6,532,071 B2 | 3/2003 | Zare et al. |
| 6,545,739 B1 | 4/2003 | Matsumoto et al. |
| 6,583,917 B2 | 6/2003 | Melloni et al. |
| 6,584,126 B2 | 6/2003 | Wang et al. |
| 6,590,710 B2 | 7/2003 | Hara et al. |
| 6,594,059 B2 | 7/2003 | Flanders |
| 6,597,713 B2 | 7/2003 | Ouchi |
| 6,608,711 B2 | 8/2003 | Flanders et al. |
| 6,627,983 B2 | 9/2003 | Tu et al. |
| 6,658,034 B2 | 12/2003 | Garnache et al. |
| 6,670,559 B2 | 12/2003 | Centola et al. |
| 6,728,286 B2 | 4/2004 | Thorland et al. |
| 6,784,946 B1 | 8/2004 | Schroter et al. |
| 6,836,501 B2 | 12/2004 | Cox et al. |
| 6,879,014 B2 | 4/2005 | Wagner et al. |
| 6,985,281 B2 | 1/2006 | Wagner et al. |
| 7,002,697 B2 | 2/2006 | Domash et al. |
| 7,012,696 B2 | 3/2006 | Orr et al. |
| 7,015,457 B2 | 3/2006 | Cole et al. |
| 7,046,326 B2 | 5/2006 | Austin et al. |
| 7,049,004 B2 | 5/2006 | Domash et al. |
| 7,050,170 B2 | 5/2006 | Chilese et al. |
| 7,089,781 B2 | 8/2006 | Petrovic et al. |
| 7,106,763 B2 | 9/2006 | Tan et al. |
| 7,113,256 B2 | 9/2006 | Butler et al. |
| 7,145,165 B2 | 12/2006 | Cox et al. |
| 7,147,165 B2 | 12/2006 | Mongin et al. |
| 7,147,695 B2 | 12/2006 | Mitra |
| 7,221,827 B2 | 5/2007 | Domash et al. |
| 7,259,856 B2 | 8/2007 | Kachanov et al. |
| 7,304,799 B2 | 12/2007 | Ma et al. |
| 7,352,463 B2 | 4/2008 | Bounaix |
| 8,068,268 B2 * | 11/2011 | Heald et al. ............ 359/290 |
| 2002/0191268 A1 | 12/2002 | Seeser et al. |
| 2003/0107739 A1 | 6/2003 | Lehmann et al. |
| 2003/0173499 A1 | 9/2003 | Cole et al. |
| 2003/0210398 A1 | 11/2003 | Augustine et al. |
| 2004/0107764 A1 | 6/2004 | Yan |
| 2004/0194628 A1 | 10/2004 | Mitra |
| 2004/0217264 A1 | 11/2004 | Wood et al. |
| 2004/0234198 A1 | 11/2004 | Wagner et al. |
| 2004/0255853 A1 | 12/2004 | Ma et al. |
| 2005/0030628 A1 | 2/2005 | Wagner et al. |
| 2005/0040337 A1 | 2/2005 | Cox et al. |
| 2005/0052653 A1 | 3/2005 | Fidric |
| 2005/0062972 A1 | 3/2005 | Krusen |
| 2005/0082480 A1 | 4/2005 | Wagner et al. |
| 2005/0094158 A1 | 5/2005 | Paldus et al. |
| 2005/0105184 A1 | 5/2005 | Ma et al. |
| 2005/0122520 A1 | 6/2005 | Yan |
| 2005/0122523 A1 | 6/2005 | Yan |
| 2005/0134836 A1 | 6/2005 | Paldus et al. |
| 2005/0254056 A1 | 11/2005 | Kachanov et al. |
| 2006/0054795 A1 | 3/2006 | Cole et al. |
| 2006/0082778 A1 | 4/2006 | Paldus et al. |
| 2006/0083284 A1 | 4/2006 | Paldus et al. |
| 2006/0084180 A1 | 4/2006 | Paldus et al. |
| 2006/0087655 A1 | 4/2006 | Augustine et al. |
| 2006/0151248 A1 | 7/2006 | Rodriguez et al. |
| 2006/0261252 A1 | 11/2006 | Cole et al. |
| 2007/0133001 A1 | 6/2007 | Cox et al. |
| 2007/0146720 A1 | 6/2007 | Cox et al. |
| 2007/0278407 A1 | 12/2007 | Wood et al. |
| 2008/0074662 A1 | 3/2008 | Gu et al. |
| 2008/0151248 A1 | 6/2008 | Cole et al. |
| 2008/0239299 A1 | 10/2008 | Cole |
| 2009/0014670 A1 | 1/2009 | Cole et al. |

FOREIGN PATENT DOCUMENTS

| | | |
|---|---|---|
| DE | 19635421 | 12/1997 |
| EP | 0 177 918 B1 | 3/1991 |
| EP | 0 667 548 A1 | 8/1995 |
| EP | 1 061 618 A2 | 12/2000 |
| EP | 1 069 658 A1 | 1/2001 |
| EP | 1 070 943 A1 | 1/2001 |
| EP | 1 847 825 A1 | 10/2007 |
| JP | 03-252172 | 11/1991 |
| JP | 05-095130 | 4/1993 |
| JP | 7-288334 A | 10/1995 |
| WO | WO 93/26049 | 12/1993 |
| WO | WO 99/42875 A1 | 8/1999 |
| WO | WO 02/04903 A1 | 1/2002 |
| WO | WO 03/098173 A1 | 11/2003 |
| WO | WO 2005/108939 A1 | 11/2005 |

OTHER PUBLICATIONS

Christian Jansen, et al., "Flexible Bragg reflectors for the terahertz regime composed of polymeric compounds", Joint 32nd International Conference on Infrared and Millimeter Waves, 2007 and the 2007 15th International Conference on Terahertz Electronics, Feb. 9, 2007, p. 984-986.

W. Henderson, et al., "Resonant Measurement Techniques Using Backward Wave Oscillators", Part of the 4th International Conference on Millimeter and Submillimeter Waves and Applications, San Diego, Jul. 1998, SPIE vol. 3465, p. 218-226.

F. Rutz, et al., "Improved dielectric mirrors for the THz frequency range", Proc. of SPIE vol. 6194 (2006), 9 pages.

Robert Schiwon, et al., "Far-infrared multilayer mirrors", Applied Physics Letters, vol. 83, No. 20, Nov. 17, 2003, p. 4119-4121.

Todd W. Du Bosq, et al., "High reflectivity intracavity Bragg mirrors for the far-infrared p-Ge laser", Proceedings of SPIE vol. 5411, (2004), p. 167-173.

Justin W. Cleary, et al., "Scanning Fabry-Perot filter for terahertz spectroscopy based on silicon dielectric mirros", Proc. of SPIE vol. 6472, (2007), 12 pages.

Justin W. Cleary, et al., "Finesse of silicon-based terahertz Fabry-Perot spectrometer", Proc. of SPIE vol. 6549, (2007), 7 pages.

Robert Schiwon, et al., "Terahertz cavity-enhanced attenuated total reflection spectroscopy", Applied Physics Letters 86, 201116 (2005), 3 pages.

Andrew C. R. Pipino, et al., "Evanescent wave cavity ring-down spectroscopy with a total-internal-reflection minicavity", Rev. Sci. Instrum. 68 (8), Aug. 1997, p. 2978-2989.

Ralph W. Bernstein, et al., "Development of a Miniature Silicon PhotoAcoustic Gas Sensor", Presented at Opto 96, Leipzig, Germany, Sep. 26-29, 1999, 6 pages.

J.D. Brown, et al., "Visible-Blind UV Digital Camera Based on a 32×32 Array of GaN/AlGaN p-i-n Photodiodes", MRS Internet Journal Nitride Semiconductor Research 4, 9 (1999), 10 pages.

Alain Campargue, et al., "Measurement of SiH2 density in a discharge by intracavity laser absorption spectroscopy and CW cavity ring-down spectroscopy", 1998, p. 1168-1175.

N. Chitica, et al., "Monolithic InP-Based Tunable Filter with 10-nm Bandwidth for Optical Data Interconnects in the 1550-nm Band", IEEE Photonics Technology Letters, vol. 11, No. 5, May 1999, p. 584-586.

Shang-I Chou, et al., "Diode-Laser Measurements of He-, Ar-, and N2-Broadened HF Lineshapes in the First Overtone Band", Journal of Molecular Spectroscopy 196 (1999), p. 70-76.

Seok-Whan Chung, et al., "Design and fabrication of 10×10 microspatial light modulator array for phase and amplitude modulation", Sensors and Actuators 78 (1999), p. 63-70.

B.R. Johnson, et al., "Microscopic Spectroscopy of Optical Mems Devices", Topic 2 (Materials and Technology), Honeywell Laboratories, around Dec. 11, 2000, 2 pages.

T.H. Edwards, "Multiple-Traverse Absorption Cell Design", Journal of the Optical Society of America, vol. 51., No. 1, Jan. 1961, p. 98-102.

A.M. Ferber, et al., "A Miniature Silicon Photoacoustic Detector for Gas Monitoring Applications", Paper Presented at the mtec 2001 International Conference on Sensors & Transducers, Birmingham, UK, Feb. 14, 2001, 7 pages.

J.H. Jerman, et al., "A miniature Fabry-Perot interferometer with a corrugated silicon diaphragm support", Sensors and Actuators—A Physical A29 (Nov. 1991) No. 2, Lausanne, CH, p. 151-158.

V.Yu. Kurochkin, et al., "Complex-cavity two-mode CO2 laser for saturated intracavity absorption", Opt. Spectrosc. (USSR) 68 (6), Jun. 1990, p. 793-797.

V.Yu. Kurochkin, et al., "Three-mirror cavity CO2 laser for intracavity saturated-absorption spectroscopy", Opt. Spectrosc. (USSR) 65 (2), Aug. 1988, p. 265-267.

Anthony O'Keefe, et al., "Cavity ring-down optical spectrometer for absorption measurements using pulsed laser sources", Review of Scientific Instruments, 59, 2544 (1988), 11 pages.

J.B. Paul, et al., "Cavity ringdown measures trace concentrations", Laser Focus World, Mar. 1997, p. 71-80.

Bruce A. Richman, et al., "Continuously tunable, single-longitudinal-mode, pulsed mid-infrared optical parametric oscillator based on periodically poled lithium niobate", 2000 Optical Society of America, vol. 17, No. 7, Jul. 2000, p. 1233-1239.

N. Sadeghi, et al., "Cavity Ring Down Spectroscopy Applied to Plasma Diagnostics", Proc. Int. Symp. Laser-aided Plasma Diagnostics, Lake Tahoe, CA, Sep. 1999, 8 pages.

J.J. Scherer, et al., "Infrared cavity ringdown laser absorption spectroscopy (IR-CRLAS) in low pressure flames", Appl. Phys. B. 64 (1997), p. 699-705.

Bill Schweber, "An Old Communications Problem Reoccurs in Optical-Communication-System Design, How it works: making the laser diode tunable", EDN, Sep. 28, 2000, p. 44-48.

Fujio Shimizu, et al., "Stark spectroscopy by 10-µ. lasers using a multipath cell", Journal of Applied Physics, vol. 46, No. 1, Jan. 1975, p. 258-259.

V.S. Smirnov, "Dye Lasers Using a Three-Mirror Cavity with Lamp Excitation", Zhurnal Prikladnoi Spektroskopii, vol. 34, No. 3, Mar. 1981, p. 275-278.

T.G. Spence, et al., "A laser-locked cavity ring-down spectrometer employing an analog detection scheme", Review of Scientific Instrucments, vol. 71, No. 2, Feb. 2000, p. 347-353.

S.M. Sze, "Physics of Semiconductor Devices", Aug. 20, 1982, 4 pages.

P. Tayebati, et al., "Microelectromechanical tunable filter with stable half symmetric cavity", Electronic Letters Online No. 19981350, Jul. 9, 1998, 2 pages.

P. Tayebati, et al., "Widely Tunable Fabry-Perot Filters using High Index-contrast DBRs", SPIE vol. 3234, 1998, p. 206-218.

Wei Yang, et al., "Back-illuminated GaN/AlGaN heterojunction photodiodes with high quantum efficiency and low noise", Applied Physics Letters, vol. 73, No. 8, Aug. 24, 1998, 5 pages.

James Allen Cox, et al., "Compact Gas Sensor Using High Reflectance Terahertz Mirror and Related System and Method", U.S. Appl. No. 12/261,823, filed Oct. 30, 2008.

* cited by examiner

HIGH REFLECTANCE TERAHERTZ MIRROR AND RELATED METHOD

TECHNICAL FIELD

This disclosure relates generally to wireless devices and more specifically to a high reflectance terahertz mirror and related method.

BACKGROUND

Gas detectors often utilize infrared detection to detect the presence and concentration of certain gases in a particular area. When a gas is in the presence of infrared light, the gas can absorb some of the infrared light's energy. Specific gases absorb infrared light at specific wavelengths, allowing the identification of gases by measuring the absorption of light at those wavelengths. Optical filters are often used to pass only particular wavelengths for a gas of interest.

Gas detectors frequently incorporate high reflectance mirrors to reflect a light signal within a measuring chamber. A light source emits a light signal, such as infrared light, towards the high reflectance mirror. The high reflectance mirror then reflects the light signal towards a detector (such as an antenna). The detector compares the amount of light transmitted through the sample of gas. The detector can therefore determine the concentration of gas present in the sample by measuring the light that passes through the sample. For example, if the amount of light transmitted through the sample is equal to that of a reference gas, the sample may not contain a gas of interest. Conversely, a measured difference between the amount of light transmitted through the sample and the reference gas can quantitatively determine the concentration of gas in the sample.

A problem with conventional high reflectance mirrors is that they can suffer from significant reflection impairment at higher frequencies. This can be a problem, for example, at frequencies of several hundred gigahertz up into the terahertz range. This reflection impairment can obstruct a proper resonance of the mirror, negatively impacting operation of a gas detector.

SUMMARY

This disclosure provides a high reflectance terahertz mirror and related method.

In a first embodiment, a method includes forming a plurality of mirror periods, stacking the mirror periods, and bonding the mirror periods together to form a high reflectance mirror. At least one of the mirror periods is formed by bonding a first semiconductor layer to a first side of a film layer (where the film layer is formed on a second semiconductor layer), forming an opening through the second semiconductor layer to expose the film layer, and cutting through the first semiconductor layer, the film layer, and the second semiconductor layer.

In a second embodiment, an apparatus includes a plurality of mirror periods stacked and bonded together. Each mirror period includes a first semiconductor layer bonded to a first side of a film layer and a second semiconductor layer bonded to a second side of the film layer. The second semiconductor layer includes an opening, and the openings in at least some of the stacked mirror periods form cavities.

In a third embodiment, a method includes forming a semiconductor structure by fusion bonding a first wafer layer to an oxide film on a second wafer layer. The method also includes forming an aperture in the second wafer layer and dicing the semiconductor structure. The method further includes stack bonding a plurality of the diced semiconductor structures to form a high reflectance mirror.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 15, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system. Also, it will be understood that elements in the figures are illustrated for simplicity and clarity and have not necessarily been drawn to scale. For example, the dimensions of some elements in the figures may be exaggerated relative to other elements to help improve the understanding of various embodiments described in this patent document.

High reflectance mirrors are often manufactured through thin film manufacturing techniques. For example, thin film manufacturing techniques can produce mirrors formed from stacks of very thin films. These mirrors work very well in the visible and infrared wavelength spectrums. The visible and infrared wavelength spectrums generally have wavelengths with magnitudes between 0.5 microns to 10 microns. Multiple stacks of quarter-wave ("$\lambda/4$") layers can be stacked using traditional techniques (such as sputtering) to grow thin films yielding very high quality. However, when the mirrors are required to operate in terahertz ("THz") frequencies, such as where the wavelengths are on the order of 100 microns, the traditional techniques often produce film thickness that are too thick.

Figure 1:
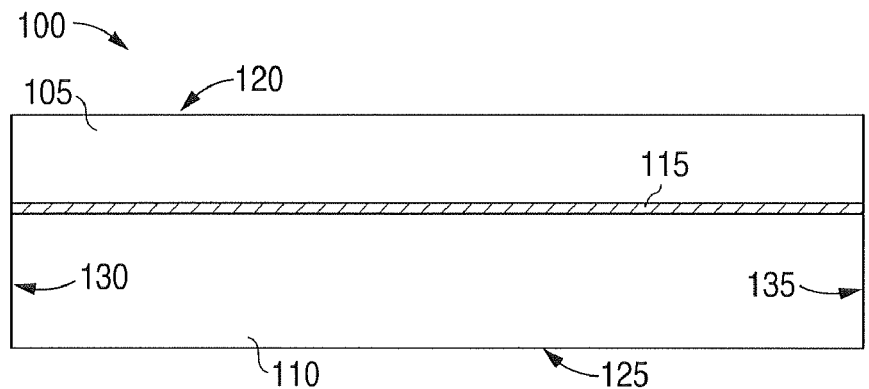
FIG. 1 illustrates an example semiconductor structure according to this disclosure.

FIG. 1 illustrates an example semiconductor structure 100 according to this disclosure. The embodiment of the semiconductor structure 100 shown in FIG. 1 is for illustration only. Other embodiments of the semiconductor structure 100 could be used without departing from the scope of this disclosure.

As described below, the semiconductor structure 100 can be used to form a mirror period to be stacked for use as a high reflectance terahertz reflective mirror. In this example, the semiconductor structure 100 includes a first semiconductor layer 105, which has a higher resistivity value (such as $>10^4$ $\Omega$ cm). The first semiconductor layer 105 could be formed from any suitable material(s). In some embodiments, the first semiconductor layer 105 represents a high resistivity silicon wafer, which could have a thickness of approximately 110 µm. The semiconductor layer 105 includes a first side (a top face) and a second side (a bottom face).

The semiconductor structure 100 also includes a second semiconductor layer 110. The second semiconductor layer 110 could be formed from any suitable material(s). Example materials include silicon, gallium arsenide, aluminum antimonide, aluminum arsenide, aluminum nitride, aluminum phosphide, boron nitride, boron phosphide, boron arsenide, gallium antimonide, gallium nitride, gallium phosphide, indium antimonide, indium arsenide, indium nitride, indium phosphide, cadmium zinc telluride, mercury cadmium telluride, mercury zinc telluride, and mercury zinc selenide. In some embodiments, the second semiconductor layer 110 represents a standard single crystal silicon wafer, which could have a thickness of approximately 125 µm. The second semiconductor layer 110 includes a front side (a top face) and a back side (a bottom face).

Silicon on insulator (SOI) wafers are made by growing an oxide layer on a wafer called the handle wafer (e.g., second semiconductor layer 110) fusion bonding the other wafer (e.g., the first semiconductor layer 105) to the handle wafer and then polishing down the handle wafer to the desired thickness. As such, the semiconductor structure 100 can be manufactured by fusion bonding the first semiconductor layer 105 and the second semiconductor layer 110 on an oxide film 115. The oxide film 115 could be approximately 0.5 µm thick. The fusion bonding can be performed so that the oxide film 115 is thermally grown onto the front side of the second semiconductor layer 110. The second side of the first semiconductor layer 105 is fusion bonded on a first face of the oxide film 115. The semiconductor structure 100 itself includes a front side 120, a back side 125, a non-bonding side 130, and a bonding side 135.

Figure 2:
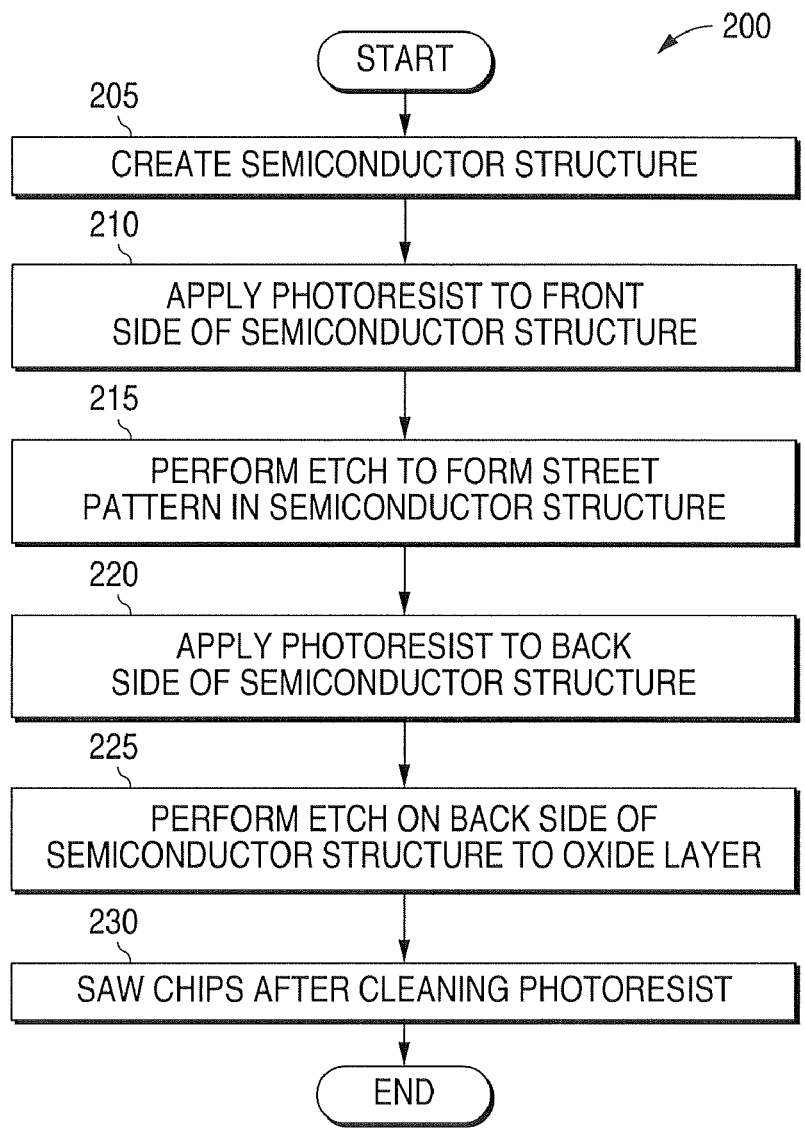
FIG. 2 illustrates an example method for manufacturing a mirror period according to this disclosure.

FIG. 2 illustrates an example method 200 for manufacturing a mirror period according to this disclosure. The embodiment of the method 200 shown in FIG. 2 is for illustration only. Other embodiments of the method 200 could be used without departing from the scope of this disclosure.

As shown in FIG. 2, the method 200 commences at step 205, where the semiconductor structure 100 is manufactured. As noted above, the semiconductor structure 100 can be assembled by fusion bonding a first semiconductor layer 105 and a second semiconductor layer 110 to an oxide film 115.

Figure 3:
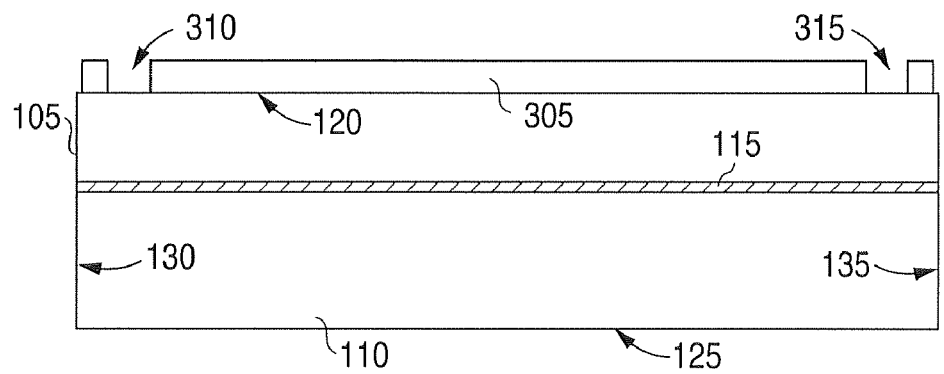
FIGS. 3 through 5, 7, and 8 illustrate an example semiconductor structure at different manufacturing stages according to this disclosure.
Figure 4:
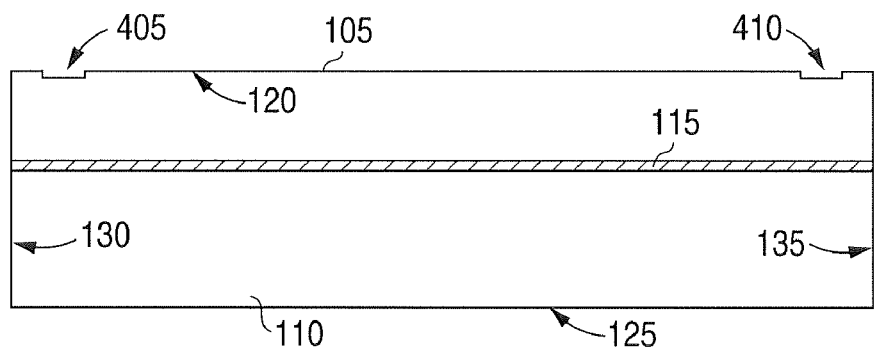

In step 210, a photoresist layer is applied to the front side 120 of the semiconductor structure 100. An example of this is shown in FIG. 3, where a photoresist layer 305 is applied to the front side 120 of the semiconductor structure 100. The photoresist layer 305 includes a pattern having a first via 310 and a second via 315. The first via 310 and the second via 315 can be formed by patterning the photoresist layer 305 using a suitable exposure. The first via 310 and the second via 315 are configured here to delineate cutting streets or sawing guides.

In step 215, an etch is perform to form a street pattern in the front side 120 of the semiconductor structure 100. The etch could represent a very short LAM etch process. The photoresist layer can be removed (such as by stripping) after the etch is performed so that substantially no portion of the photoresist layer remains on the semiconductor structure 100. This produces the structure shown in FIG. 4, where a first street pattern 405 and a second street pattern 410 are formed in the front side 120 of the semiconductor structure 100.

Figure 5:
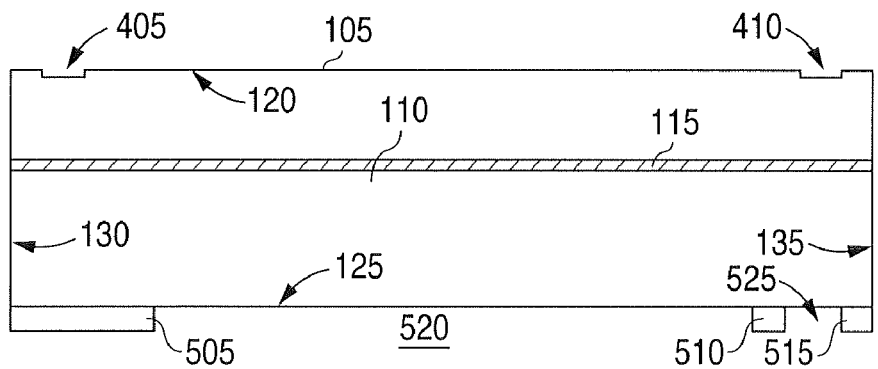

In step 220, a photoresist layer is applied to the back side 125 of the semiconductor structure 100. An example of this is shown in FIG. 5, where a photoresist layer 505, 510 and 515 is applied to the back side 125 of the semiconductor structure 100. The photoresist layer 505, 510 and 515 could be formed in any suitable manner and using any suitable material(s), such as forming a 4,000 Å layer of aluminum using an MA-6 mask aligner. As shown in FIG. 5, the photoresist layer 505, 510 and 515 delineates a window area 520, a glue ledge area 525 and optionally a weep hole (not specifically illustrated) (to allow pressure equilibration between the air chambers after the chips are stacked together). In particular embodiments, the window area 520 can be 1.25 cm to 1.75 cm wide, such as approximately 1.5 cm wide.

Figure 6A:
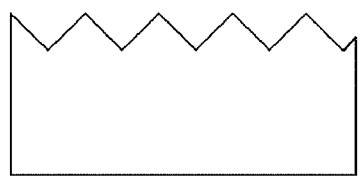
FIGS. 6A and 6B illustrate example etching processes according to this disclosure.
Figure 6B:
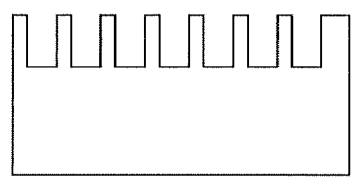
Figure 7:
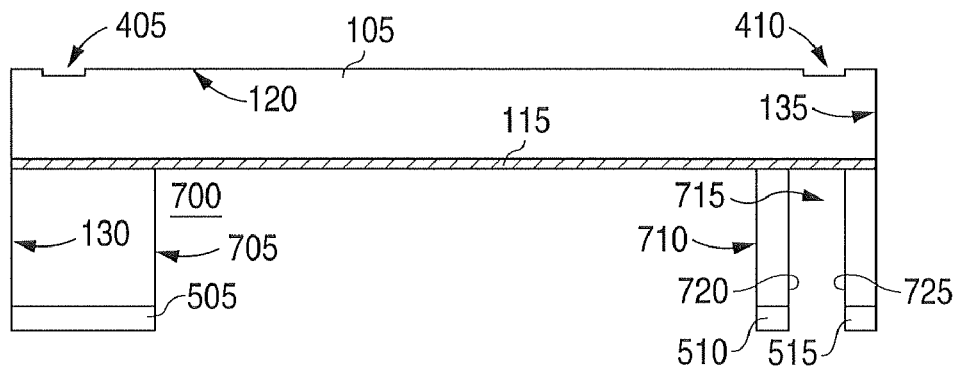

In step 225, an etch is perform on the back side 125 of the semiconductor structure 100 to etch through to the oxide film 115. FIG. 6A illustrates example results produced using a wet etch, while FIG. 6B illustrates example results produced by a deep reactive ion etch ("DRIE"). DRIE is highly anisotropic, while wet etching could yield a profile with 54° (from normal). DRIE etching yields profiles with nearly 90° or perpendicular to the surface. In some embodiments, the etching performed at step 225 is a DRIE etch performed on the back side 125 of the semiconductor structure 100. The results of the etch are shown in FIG. 7, where the DRIE etch has created a notch 700. The notch 700 represents a wide passage to the oxide film 115 through the second semiconductor layer 110. The DRIE etch can naturally terminate at the oxide film 115, helping to increase accuracy and obtain uniform thickness. The notch 700 here is defined by a first sidewall 705 and a second sidewall 710. The notch 700 could be between 1.25 cm to 1.75 cm wide (such as 1.5 cm wide) between its sidewalls. A second notch 715 is also formed in the second semiconductor layer 110 during the DRIE etch. The second notch 715 is defined by a third sidewall 720 and a fourth sidewall 725. Once the etch is complete, the photoresist layer 505, 510 and 515 can be removed (such as by stripping) so that substantially none of the photoresist layer 505, 510 and 515 remains on the semiconductor structure 100.

Figure 8:
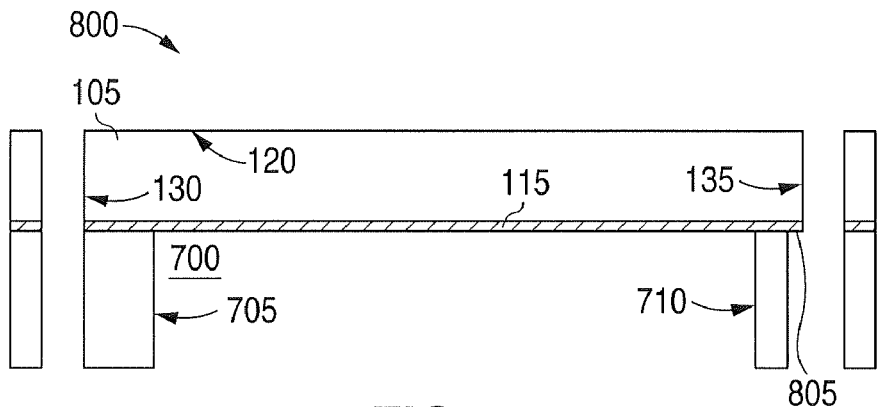

In step 230, the semiconductor structure 100 is diced or cut along the first street pattern 405 and the second street pattern 410. As shown in FIG. 8, cutting along the first street pattern 405 and the second street pattern 410 yields a mirror period 800. Also, a glue ledge 805 is formed on the bonding side 135 of the mirror period 800. The glue ledge 805 may be formed, for example, due to the MA-6 mask aligner aligning the second street pattern 410 with the fourth sidewall 725. This completes the formation of the mirror period 800 as described in FIG. 2.

Figure 9:
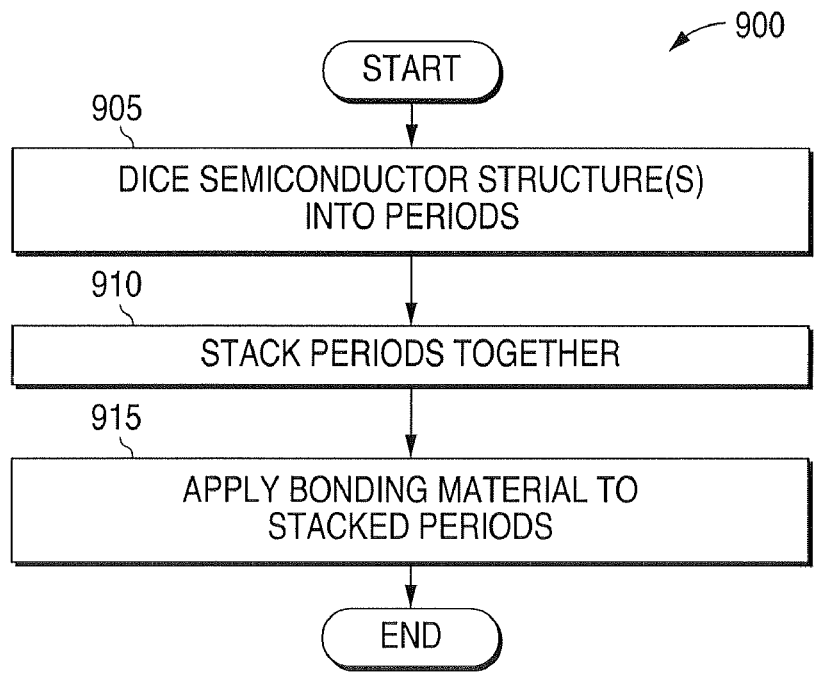
FIG. 9 illustrates an example method for stack bonding mirror periods into a terahertz high reflectance mirror according to this disclosure.

FIG. 9 illustrates an example method 900 for stack bonding mirror periods into a terahertz high reflectance mirror according to this disclosure. The embodiment of the method 900 shown in FIG. 9 is for illustration only. Other embodiments of the method 900 could be used without departing from the scope of this disclosure.

Figure 10:
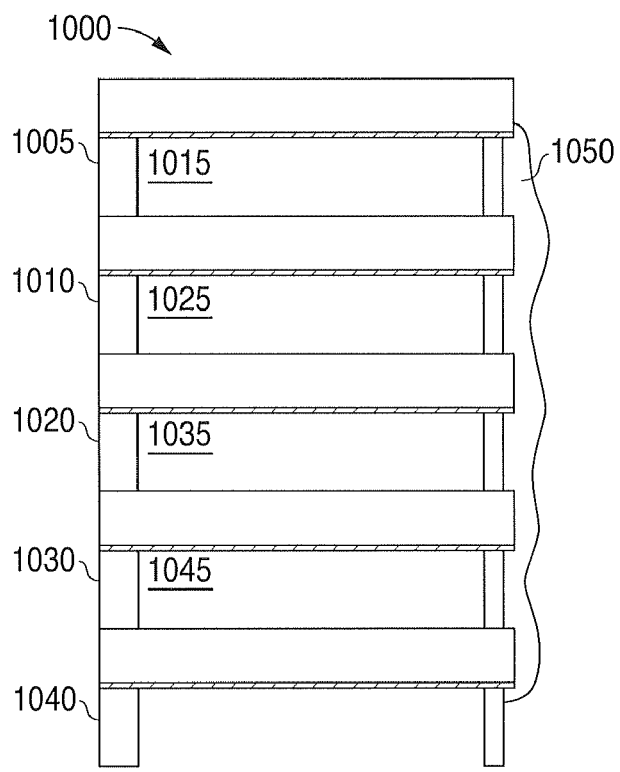
FIG. 10 illustrates an example terahertz high reflectance mirror according to this disclosure.

Multiple periods (such as at least five periods) from one or more semiconductor structure 100 are formed at step 905, such as by using the method 200 of FIG. 2. The periods are then stacked at step 905, an example of which is shown in FIG. 10. As shown in FIG. 10, a first period 1005 is stacked on top of a second period 1010 such that the back side 125 of the first period 1005 is placed adjacent to the front side 120 of the second period 1010. The notch 700 of the first period 1005 and the front side 120 of the second period 1010 form a first period cavity 1015. Similar steps can be used to stack additional periods 1020, 1030, 1040 to form period cavities 1025, 1035, 1045. At step 915, a bonding material 1050 is applied to the stacked periods, forming a completed mirror 1000.

In this example, the mirror 1000 represents a five-period high reflectance terahertz reflective mirror. In particular embodiments, the periods in the mirror 1000 could be formed from high-resistivity (hi-ρ) silicon and air. The refractive index n of silicon is 3.418 at 300K, and the refractive index for air is "1." Table 1 illustrates the refractive index and optical thickness of high resistivity silicon (Si), silicon dioxide ($SiO_2$), and air.

TABLE 1

|  | Si |  | $SiO_2$ |  | Air |
|---|---|---|---|---|---|
| OPL | $\lambda/4$ | $3\lambda/4$ | ,0 $\lambda/4$ | $3\lambda/4$ | $\lambda/4$ |
| d (μm) | 36.57 | 109.7 | 86.21 | 258.6 | 125 |
| n | 3.418 |  | 1.95 + i0.008 | 1 | 1 |

In some embodiments, the first semiconductor layer 105 is between 105 μm and 115 μm thick, and the period cavity is between 120 μm and 130 μm thick. In particular embodiments, the mirror 1000 could include a quarter-wave silicon film and a quarter-wave air design. In these embodiments, the first semiconductor layer 105 in each mirror period can be approximately 37 μm thick, and each period cavity could be 1.5 cm in width and 125 μm in height. In other particular embodiments, the mirror 1000 could include a three-quarter-wave silicon film and a quarter-wave air design. In those embodiments, the first semiconductor layer 105 in each mirror period can be 110 μm thick, and each period cavity could be 1.5 cm in width and 125 μm in height. Here, the thickness tolerances could be less than 10 μm.

Figure 11A:
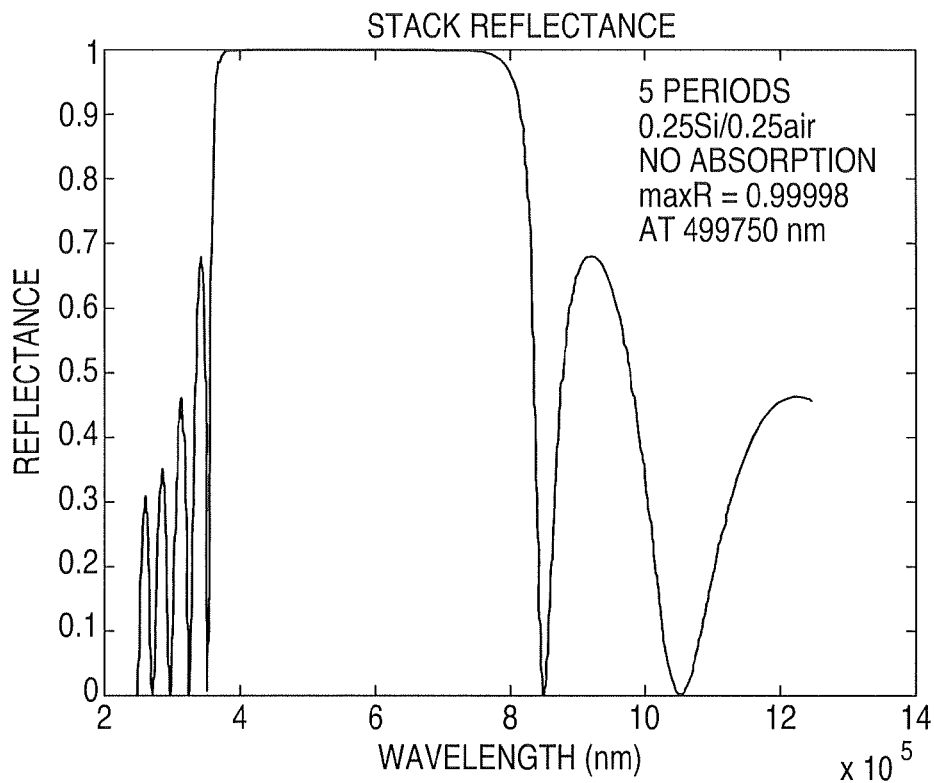
FIGS. 11A and 11B illustrate graphs of example reflectances of a terahertz mirror according to this disclosure.
Figure 11B:
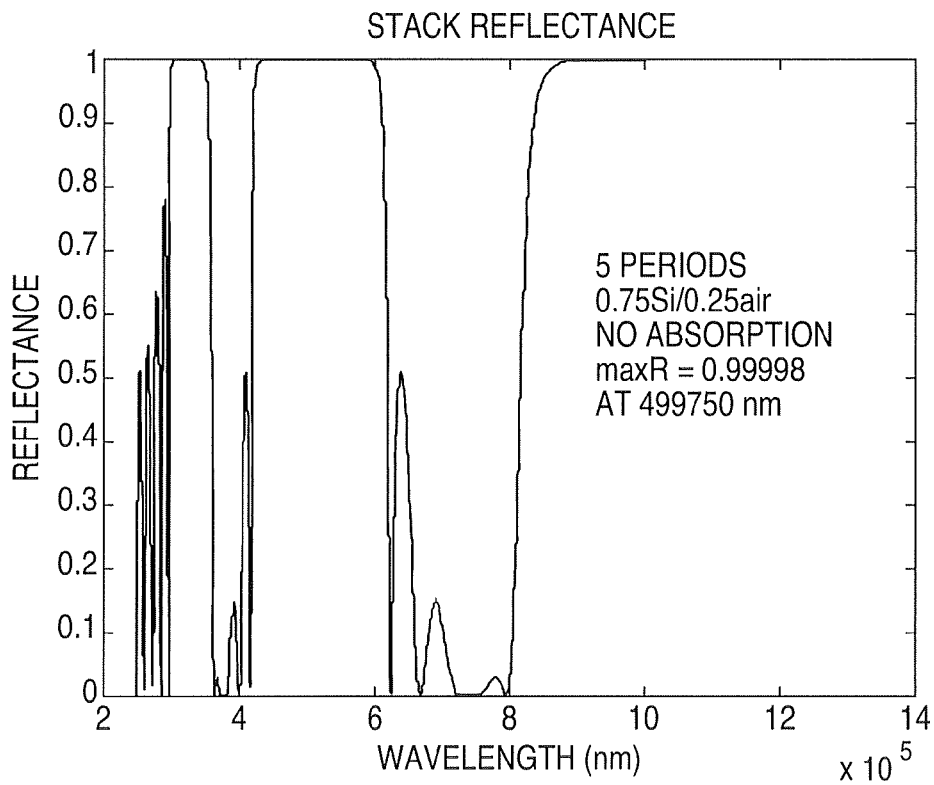

FIGS. 11A and 11B illustrate graphs of example reflectances of a terahertz mirror according to this disclosure. In particular, FIG. 11A illustrates a graph of the reflectance of the mirror 1000 that includes a quarter-wave silicon film and a quarter-wave air layer. FIG. 11B illustrates a graph of the reflectance of the mirror 1000 that includes a three-quarter-wave silicon film and a quarter-wave air layer. In these examples, no absorption value was utilized (K=0), and both embodiments yield a maximum reflectance ("max R") of nines to a fifth decimal place (also called "five nines reflectance").

In particular embodiments, the mirror 1000 can be manufactured using MEMS processing. Also, each mirror period 1005, 1010, 1020, 1030, 1040 could include a basic high-index|low-index mirror period, such as high resistivity silicon (n=3.418) and air (n=1) (although any other suitable material or materials could be used).

Figure 12:
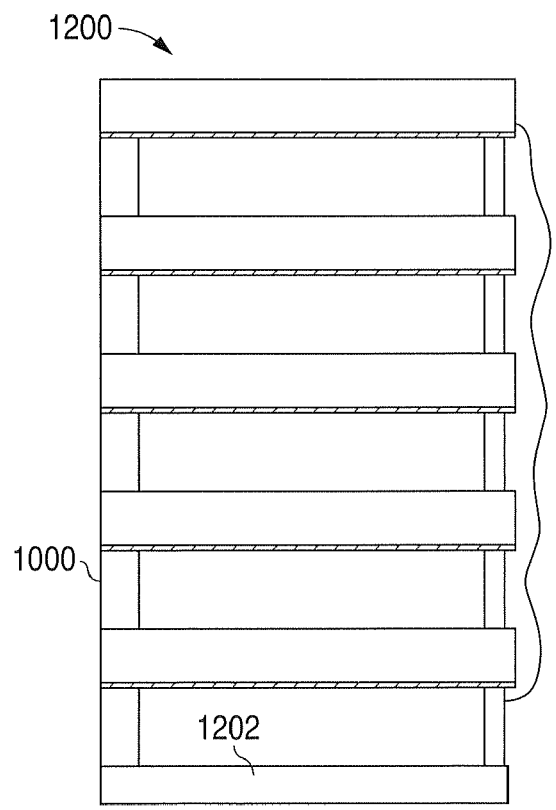
FIG. 12 illustrates another example terahertz high reflectance mirror according to this disclosure.

FIG. 12 illustrates another example terahertz high reflectance mirror 1200 according to this disclosure. The embodiment of the mirror 1200 shown in FIG. 12 is for illustration only. Other embodiments of the mirror 1200 could be used without departing from the scope of this disclosure.

In this example, the mirror 1200 includes the same general structure as the mirror 1000. In addition, the mirror 1200 includes a spacer layer 1202, which could be formed from any suitable material(s) like high quality fused silica ($SiO_2$). The spacer layer 1202 can be used to separate the period cavity within the bottom mirror period and an underlying substrate. For $SiO_2$, the value of n used could be 1.95+i0.008. In other embodiments, the spacer layer 1202 could be silicon.

Although these figures have illustrated two example terahertz high reflectance mirrors and various structures and methods for fabricating the terahertz high reflectance mirrors, various changes may be made to these figures. For example, a terahertz high reflectance mirror could include any suitable number of mirror periods. Also, a terahertz high reflectance mirror could be fabricated using any suitable structures and any suitable series of processing operations (such as photoresist patterning, etches, and sawing).

Figure 13:
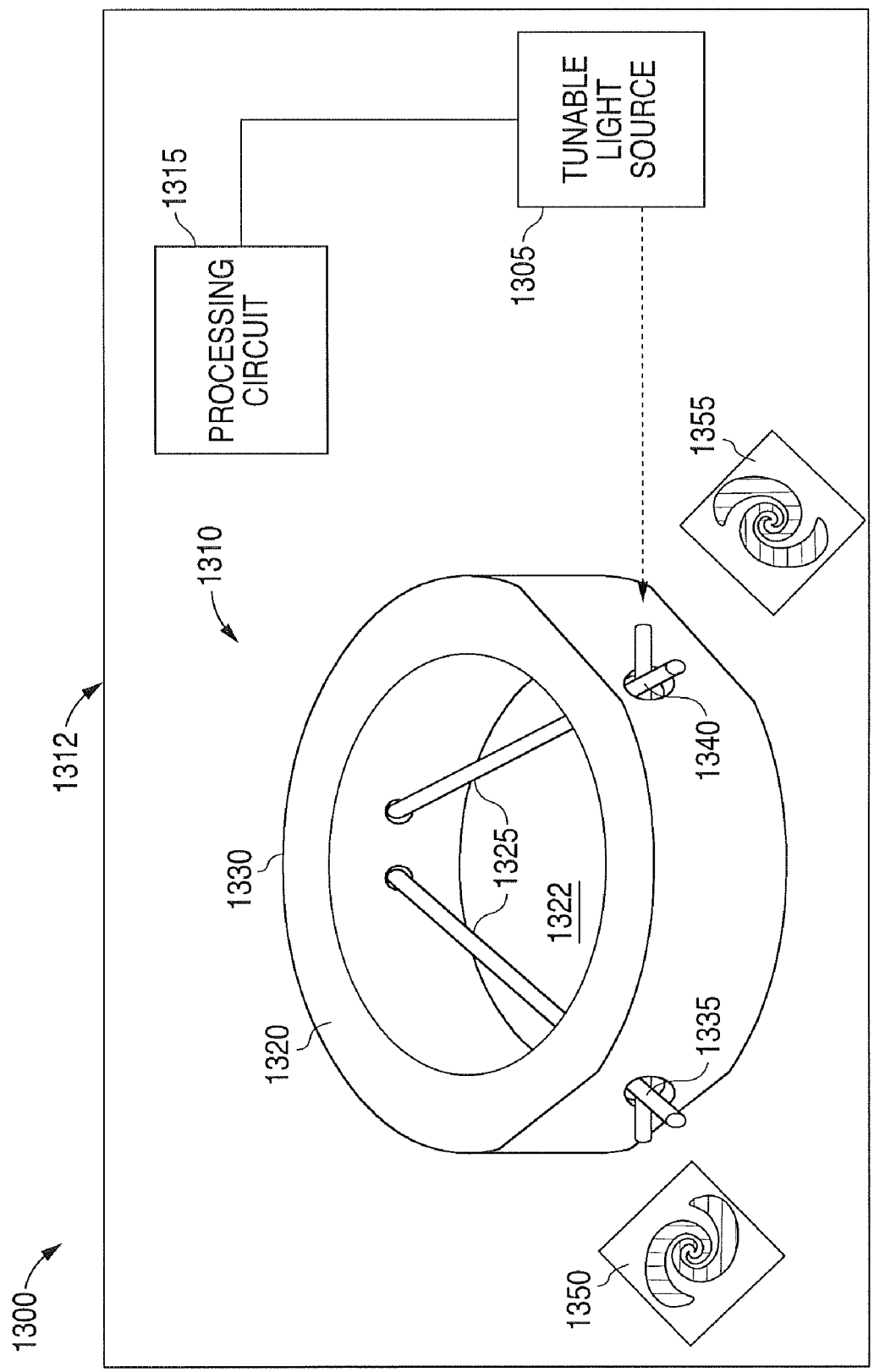
FIG. 13 illustrates an example gas detection system according to this disclosure.

FIG. 13 illustrates an example gas detection system 1300 according to this disclosure. The embodiment of the gas detection system 1300 shown in FIG. 13 is for illustration only. Other embodiments of the gas detection system 1300 could be used without departing from the scope of this disclosure.

In this example, the gas detection system 1300 includes a tunable light source 1305 and gas detection cell 1310. In some embodiments, the tunable light source 1305 and the gas detection cell 1310 are contained within a housing 1312. In other embodiments, the tunable light source 1305 and the gas detection cell 1310 are not contained within the same housing.

The tunable light source 1305 represents any suitable tunable signal source, such as a monochromatic terahertz light source. For example, the tunable light source 1305 could be operable to emit light at a wavelength between 100 GHz and 10,000 GHz. The tunable light source 1305 can also adjust the wavelength of the emitted light. In some embodiments, the tunable light source 1305 is coupled to a processing circuit 1315, which can control the tuning of the tunable light source 1305. The processing circuit 1315 could tune the light source 1305 in any suitable manner, such as in response to operator input or based on software/firmware instructions. In particular embodiments, the tunable light source 1305 represents a backward wave oscillator ("BWO"). The processing circuit 1315 includes any suitable processing or computing device for controlling a tunable light source.

In this example, the gas detection cell 1310 includes a resonant cavity 1320, which includes a gas chamber 1322. The gas chamber 1322 is an area containing a gas or gases. The light emitted by the tunable light source 1305 traverses an absorption path through the gas chamber 1322. As the light traverses the absorption path through the gas chamber 1322, portions of light energy are absorbed by the gas or gases present in the gas chamber 1322.

The gas detection cell 1310 also includes at least one high reflectance terahertz mirror 1330 (located on the far side of the resonant cavity 1320 in FIG. 13). The high reflectance terahertz mirror 1330 could, for example, represent a mirror as shown in FIG. 10 or FIG. 12 and described above. The gas detection cell 1310 further includes a first terahertz detector 1350 and a second terahertz detector 1355.

In some embodiments, the high reflectance terahertz mirror 1330 is mounted on a piezo-transducer and a position actuator. The terahertz mirror 1330 can also be coupled to the processing circuit 1315. The actuator for the terahertz mirror 1330 can be controlled by the processing circuit 1315 to vary an angle of incidence of reflected light. This can be done to adjust the absorption path length of the cavity resonance based on the frequency of the light emitted from the tunable light source 1305. The processing circuit 1315 can therefore tune the resonant cavity 1320 by varying the angle of incidence of the terahertz mirror 1330, such as by varying the angle of incidence so that a Fabry-Perot resonance is achieved. The processing circuit 1315 can also tune the resonant cavity 1320 in any suitable manner, such as based on operator input, software/firmware instructions, or signals received from the piezo-transducer.

Depending on the implementation, the gas detection cell 1310 could include a second terahertz mirror 1335 and possibly a third terahertz mirror 1340. If two terahertz mirrors 1330-1335 are used, the gas detection cell 1310 could be linear in shape. If three terahertz mirrors 1330-1340 are used, the resonant cavity 1320 can be a closed triangular absorption cavity. In embodiments where three terahertz mirrors 1330-1340 are used, each leg 1325 of the resonant cavity 1320 can be 10 cm in length to create a physical absorption path of thirty centimeters (30 cm). This could allow the gas detection cell 1310 and the tunable light source 1305 to fit within one cubic foot (1 ft$^3$). Also, in these embodiments, the processing circuit 1315 can be configured to optimize the gas detection system 1300, such as by tuning the resonant cavity 1320 by varying the angle of incidence of the terahertz mirror 1330 based on the frequency of the light source 1305 until a Fabry-Perot resonance is achieved within the resonant cavity 1320.

The use of the terahertz mirrors 1330-1340, which can have a reflectance greater than 0.999 in the gas detection cell 1310, can effectively increase the absorption path length by a large amount. As a particular example, the absorption path length could be increased by approximately one thousand times, such as by increasing the absorption path length from 0.5 m to 1000 m. Accordingly, the gas detection system 1300 can be quite compact and achieve a high sensitivity (such as parts per billion) in a small volume.

In this example, the first terahertz detector 1350 is configured to detect a transmitted signal from the tunable light source 1305. The second terahertz detector 1355 is configured to detect a reflected signal from one or more of the terahertz mirrors 1330-1340. The terahertz detectors 1350-1355 may represent uncooled, high sensitivity detectors, and each can include a MEMS microbridge with a noise equivalent power less than 10 pW/√Hz (NEP<10 pW/√Hz) and a 100 μs response. In some embodiments, the terahertz detectors 1350-1355 could each include a Schottky-barrier diode with a 1 ns response for cavity ring-down spectroscopy methods.

Note that the embodiment of the gas detection cell 1310 shown in FIG. 13 is for illustration only. Other embodiments of the gas detection cell 1310 could be used. In particular, one or more terahertz mirrors could be used in any suitable gas detection cell.

FIGS. 14A through 14F illustrate example absorption peaks of gases of interests according to this disclosure. The gases shown here are for illustration only. Other gases with their associated absorption peaks could also be detected.

Figure 14A:
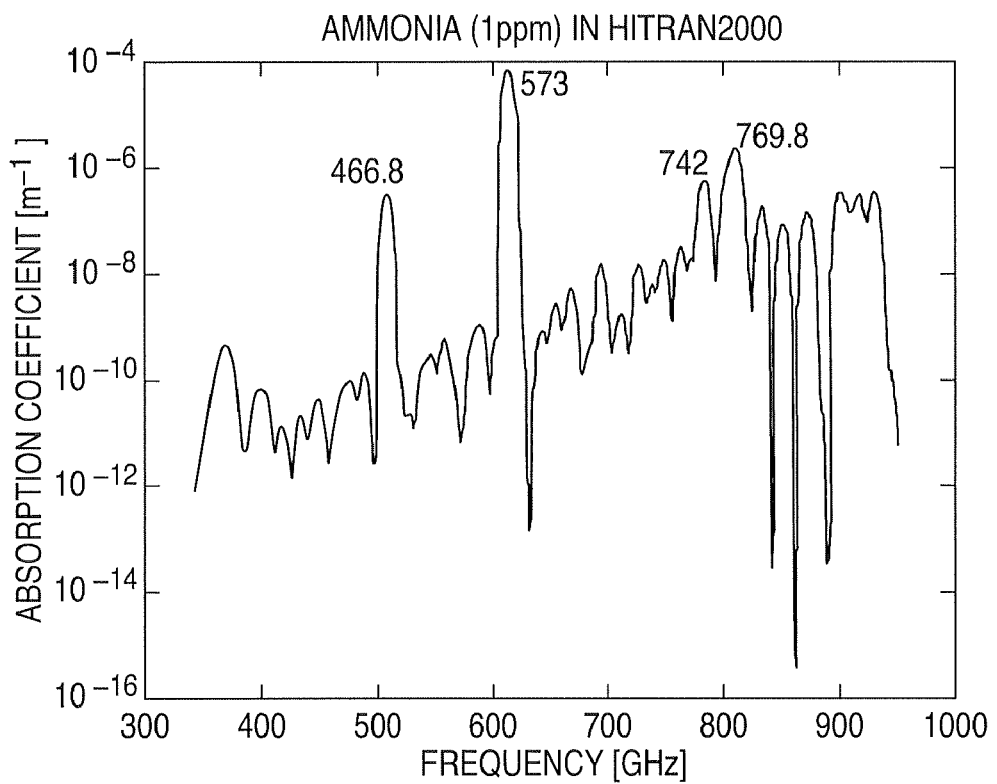
FIGS. 14A through 14F illustrate example absorption peaks of gases of interests according to this disclosure.
Figure 14B:
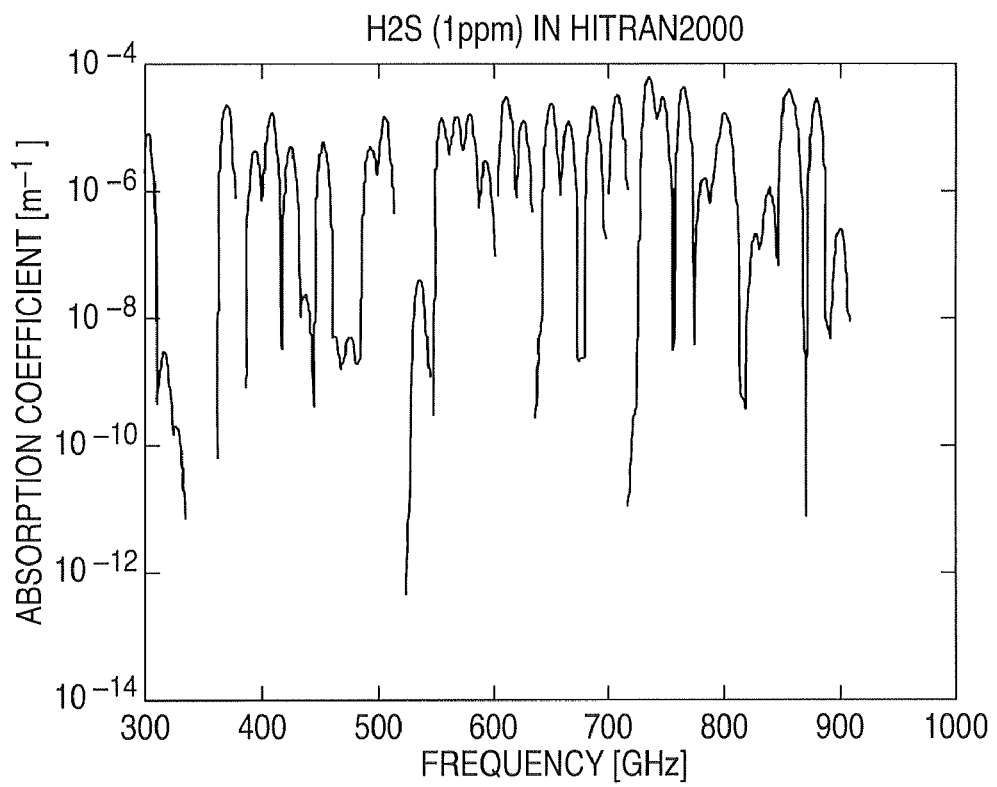
Figure 14C:
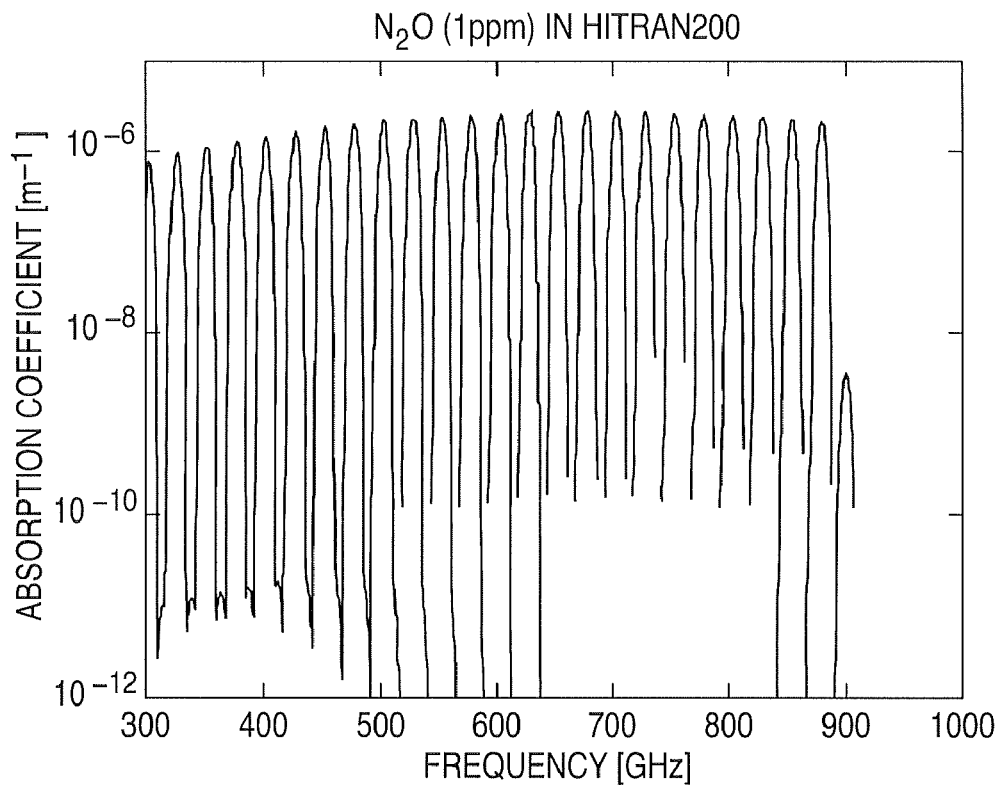
Figure 14D:
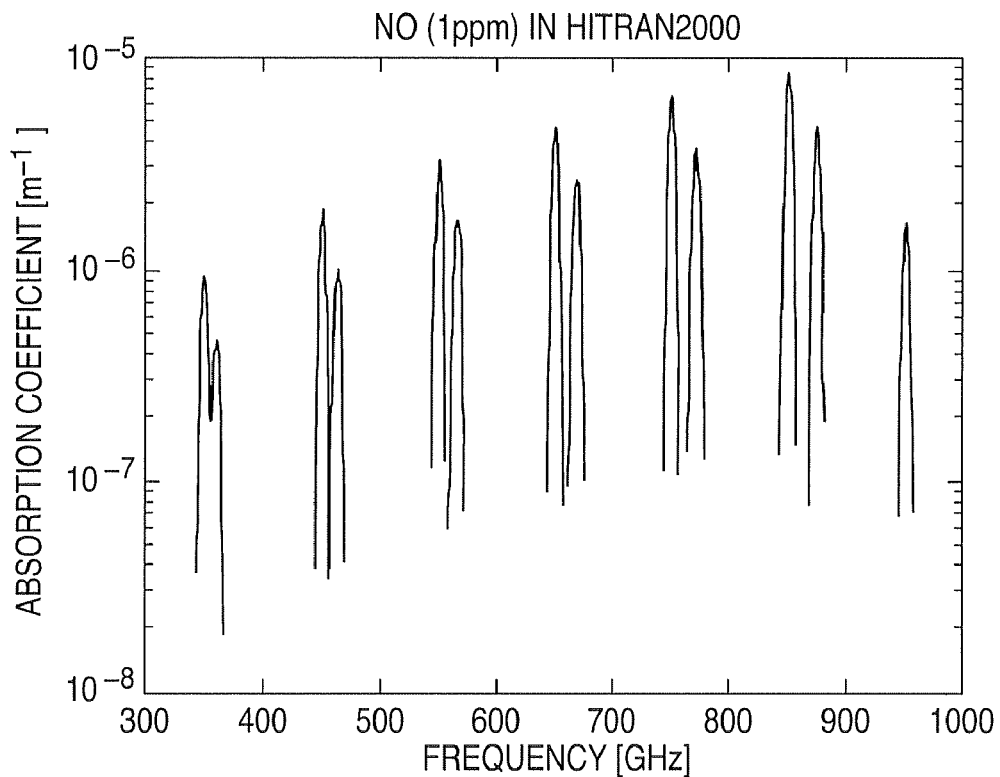
Figure 14E:
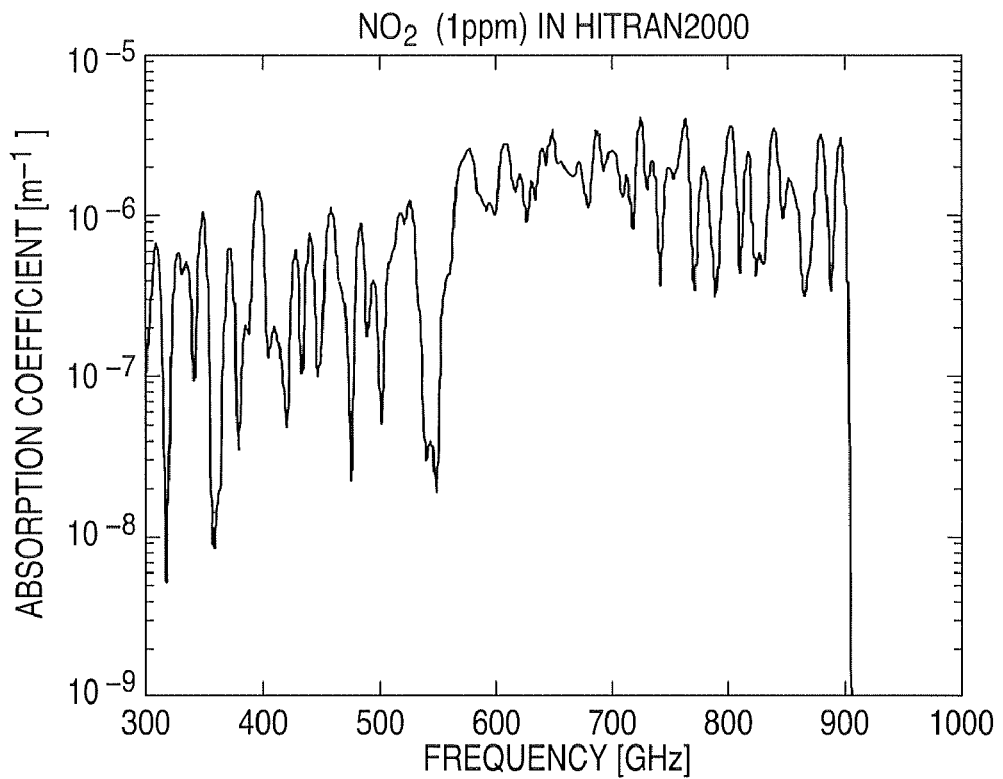
Figure 14F:
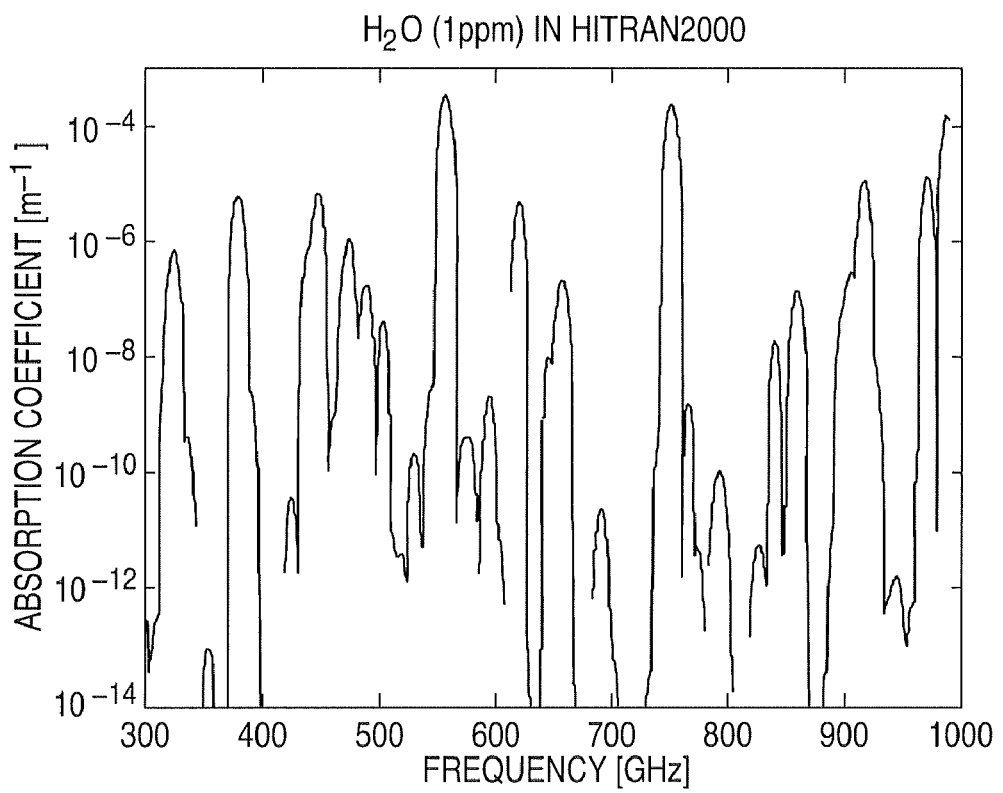

FIG. 14A illustrates the absorption peaks of ammonia. FIG. 14B illustrates the absorption peaks of hydrogen sulfide. FIG. 14C illustrates the absorption peaks of nitrous oxide. FIG. 14D illustrates the absorption peaks of nitrogen oxide. FIG. 14E illustrates the absorption peaks of nitrogen dioxide. FIG. 14F illustrates the absorption peaks of water. Absorption peaks, as illustrated in FIGS. 14A through 14F, are typically unique to gases of interest.

These absorption peaks can be used by the gas detection system 1300 to determine if any of these gases are present in a sample. For example, the gas detection system 1300 can compare the transmitted signal detected by the first detector 1350 (the signal transmitted from the light source 1305) to the signal detected by the second detector 1355 (the reflected signal). The gas detection system 1300 can use this to determine an absorption of the light signal based on the comparison of the transmitted and reflected signals. The gas detection system 1300 can then identify the gas or gases present based on the absorption of the light signal at the frequency or frequencies generated by the light source 1305. Accordingly, the gas detection system 1300 is operable to determine the presence of a gas within the gas detection cell 1310.

Figure 15:
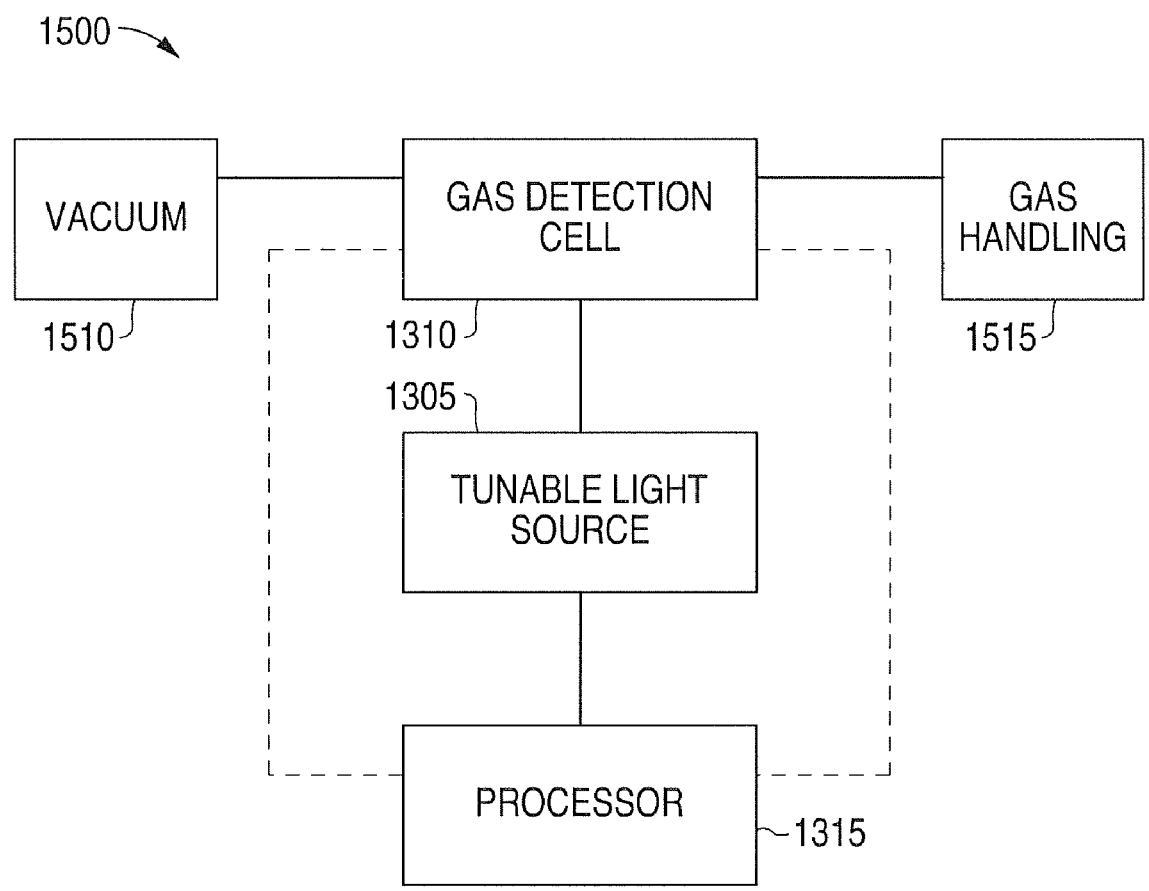
FIG. 15 illustrates another example gas detection system according to this disclosure.

FIG. 15 illustrates another example gas detection system 1500 according to this disclosure. The embodiment of the gas detection system 1500 shown in FIG. 15 is for illustration only. Other embodiments of the gas detection system 1500 could be used without departing from the scope of this disclosure.

In this example, the gas detection system 1500 includes the same general structure as the gas detection system 1300. In addition, to eliminate possible overlap of absorption peaks of certain gases due to pressure broadening, the gas detection system 1500 can operate at reduced pressure, such as between one thousandth to one hundredth of an atmosphere ($10^{-3}$ to $10^{-4}$ atmosphere). The gas detection system 1500 is coupled to vacuum equipment 1510 and gas handling equipment 1515. The vacuum equipment 1510 is operable to reduce a pressure in the gas detection cell 1310, and the gas handling equipment 1515 is operable to introduce gas to be measured into the gas detection cell 1310.

Although these figures have illustrated two example gas detection systems and various absorption peaks detected, various changes may be made to these figures. For example, the gas detection cell could have any suitable configuration, such as linear or pentagonal, and can include any number of high reflectance terahertz mirrors. Also, more than one high reflectance terahertz mirror may be mounted on a position actuator. In these embodiments, the processing circuit 1315 can tune the resonant cavity 1320 by varying the angle of incidence of one or more of the terahertz mirrors. In addition, the tunable light source 1305 could represent a laser, such as a gas laser, or any other suitable tunable light source.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   forming a plurality of mirror periods, wherein at least one of the mirror periods is formed by:
   bonding a first semiconductor layer to a first side of a film layer, a second semiconductor layer bonded to a second side of the film layer opposite the first side;

forming an opening through the second semiconductor layer to expose the film layer and form a notch in the second semiconductor layer, wherein remaining portions of the second semiconductor layer form sidewalls of the notch; and cutting through the first semiconductor layer, the film layer, and the second semiconductor layer;

stacking the mirror periods; and bonding the mirror periods together to form a high reflectance mirror, the notch in the at least one mirror period forming a cavity when the mirror periods are bonded together.

2. The method of claim 1, wherein at least one of the mirror periods is formed further by:

depositing a photoresist layer over the first semiconductor layer, the photoresist layer including two vias; and etching the first semiconductor layer through the vias to form street patterns in the first semiconductor layer.

3. The method of claim 2, wherein cutting through the first semiconductor layer, the film layer, and the second semiconductor layer comprises cutting along the street patterns in the first semiconductor layer.

4. The method of claim 1, wherein forming the opening through the second semiconductor layer comprises:

depositing a photoresist layer over the second semiconductor layer, the photoresist layer including a first open area; and etching the second semiconductor layer through the first open area to form the opening.

5. The method of claim 4, wherein:

the photoresist layer further includes a second open area;

etching the second semiconductor layer and cutting through the first semiconductor layer, the film layer, and the second semiconductor layer form a glue notch; and bonding the plurality of mirror periods together comprises depositing a bonding material along the glue notches of the mirror periods.

6. The method of claim 1, wherein:

the first semiconductor layer comprises a high resistivity silicon wafer;

the film layer comprises an oxide film; and the second semiconductor layer comprises a silicon wafer.

7. The method of claim 6, wherein:

the high resistivity silicon wafer is approximately 110 μm thick; and the silicon wafer is approximately 125 μm thick.

8. The method of claim 1, wherein the opening through the second semiconductor layer is 1.25 cm to 1.75 cm in width.

9. The method of claim 1, further comprising:

a spacer layer formed under a bottom one of the stacked mirror periods.

10. The method of claim 1, wherein forming the opening through the second semiconductor layer comprises performing a deep reactive ion etch.

11. The method of claim 1, wherein forming the opening through the second semiconductor layer exposes the film layer without etching through the film layer.

12. The method claim 1, wherein:

cutting through the first semiconductor layer, the film layer, and the second semiconductor layer comprises cutting through the first semiconductor layer, the film layer, and the second semiconductor layer in a first direction; and forming the opening through the second semiconductor layer comprises etching through the second semiconductor layer in a second direction opposite the first direction.

13. The method of claim 1, further comprising:

forming a weep hole though the second semiconductor layer; and using the weep hole to achieve pressure equilibration between adjacent mirror periods when the mirror periods are bonded together.

14. An apparatus comprising:

a plurality of mirror periods stacked and bonded together, each mirror period comprising:

a first semiconductor layer bonded to a first side of a film layer; and a second semiconductor layer bonded to a second side of the film layer opposite the first side, the second semiconductor layer comprising an opening that exposes the film layer and forms a notch in the second semiconductor layer, wherein remaining portions of the second semiconductor layer form sidewalls of the notch;

wherein the notches in at least some of the stacked mirror periods form cavities.

15. The apparatus of claim 14, wherein the first semiconductor layer in each mirror period has a high refractive index and material in the cavity of each mirror period has a low refractive index, giving the apparatus a high-index|low-index mirror period.

16. The apparatus of claim 14, wherein:

each mirror period further comprises a glue notch along its side; and the mirror periods are bonded together by a bonding material deposited along the glue notches of the mirror periods.

17. The apparatus of claim 14, wherein:

the first semiconductor layer in each mirror period comprises a high resistivity silicon wafer;

the film layer in each mirror period comprises an oxide film; and the second semiconductor layer in each mirror period comprises a silicon wafer.

18. The apparatus of claim 17, wherein:

the high resistivity silicon wafer in each mirror period is approximately 110 μm thick; and the silicon wafer in each mirror period is approximately 125 μm thick.

19. The apparatus of claim 14, wherein the opening through the second semiconductor layer in each mirror period is 1.25 cm to 1.75 cm in width.

20. The apparatus of claim 14, further comprising:

a spacer layer under a bottom one of the stacked mirror periods.

21. The apparatus of claim 14, wherein the cavity in each mirror period comprises air.

22. A method comprising:

forming a semiconductor structure by fusion bonding a first wafer layer to a first side of an oxide film, a second wafer layer bonded to a second side of the oxide film opposite the first side;

forming an aperture through the second wafer layer to expose the oxide film and form a notch in the second wafer layer, wherein remaining portions of the second wafer layer form sidewalls of the notch;

dicing the semiconductor structure; and stack bonding a plurality of the diced semiconductor structures to form a high reflectance mirror, the notch in at least one diced semiconductor structure forming a cavity when the diced semiconductor structures are stack bonded.

23. The method of claim 22, wherein the first wafer layer comprises a high resistivity silicon wafer.

* * * * *